United States Patent [19]
Hed

[11] Patent Number: 5,139,496
[45] Date of Patent: Aug. 18, 1992

[54] ULTRASONIC FREEZE ABLATION CATHETERS AND PROBES

[76] Inventor: Aharon Z. Hed, 12 Wagon Trail Dr., Nashua, N.H. 03062

[21] Appl. No.: 630,532

[22] Filed: Dec. 20, 1990

[51] Int. Cl.⁵ ............................................. A61B 17/36
[52] U.S. Cl. ..................................... 606/23; 606/21; 606/24
[58] Field of Search ................................ 606/20–26; 62/51.2, 52.1, 293

[56] References Cited

U.S. PATENT DOCUMENTS

| | | | |
|---|---|---|---|
| 3,298,371 | 1/1967 | Lee | 606/23 |
| 3,502,081 | 3/1970 | Amoils | 606/24 |
| 3,696,813 | 10/1972 | Wallach | 606/26 |
| 3,782,386 | 1/1974 | Barger et al. | 606/23 |
| 3,913,581 | 10/1975 | Ritson et al. | 606/23 |
| 4,202,336 | 5/1980 | van Gerven | 606/21 |
| 4,275,734 | 6/1981 | Mitchiner | 606/23 |
| 4,528,979 | 7/1985 | Marchenko et al. | 606/21 |
| 4,946,460 | 8/1990 | Merry et al. | 606/24 |

FOREIGN PATENT DOCUMENTS

| | | |
|---|---|---|
| 0769814 | 7/1981 | U.S.S.R. . |
| 1138146 | 2/1985 | U.S.S.R. . |
| 1258394 | 9/1986 | U.S.S.R. . |
| 1266532 | 10/1986 | U.S.S.R. . |

Primary Examiner—Peter A. Aschenbrenner
Attorney, Agent, or Firm—Eliot S. Gerber

[57] ABSTRACT

Probes for medical surgery and flexible catheters for internal tissue ablation in which the tissue cells are frozen and deadened and yet extreme supercooling of tissue below the tissues' melting point is not required. The tissue cells are moderately supercooled by the probe or catheter and freezing of the cells is caused by cavitation nucleation of ice particles within the cells induced by a low power ultrasonic wave generator. The ultrasonic energy causes well distributed nucleation in the supercooled tissue cells and, as a result, the cells rapidly freeze and, due to such freezing, expand and burst their membranes.

15 Claims, 5 Drawing Sheets

ULTRASONIC FREEZE ABLATION CATHETERS AND PROBES

BACKGROUND OF THE INVENTION

1. Field of the Invention

This invention relates to the medical instrument field and more particularly to catheters and probes which cause the freezing of tissue cells.

2. Related Art

Cryogenic devices for surgical applications have been described in the patent literature. Generally, the cold tissue is at least below −60° C. and often below cryogenic temperature (below −150° C.). For instance, A. S. J. Lee (U.S. Pat. No. 3,298,371) describes a liquid nitrogen freezing probe that can be used for stereotaxic neurosurgery in which selected tissues are deadened. In other devices, the use of Joule-Thomson valves to obtain cryogenic cooling in cryosurgical instruments is empoyed (for instance, U.S. Pat. Nos. 3,502,081 and 3,696,813). Later developments, which are aimed at resolving problems of reproducibility of necrosis (the deadening of cells) and release of the frozen tip from the frozen tissues by rewarming the cryogenic tip, are described in U.S. Pat. No. 3,782,386, its reissue U.S. Pat. No. Re 28,657, and U.S. Pat. Nos. 3,913,581 and 4,202,336.

The mechanism involved in cryogenic cell deadening is believed to involve the freezing of the internal cellular matter, expansion of the frozen cellular matter and the consequent rupture of the cell's membranes. The prior art indicates that cryogenic cell deadening requires very rapid supercooling of the ablated tissues. According to Robert K. Mitchiner (U.S. Pat. No. 4,275,734, which is incorporated herein by reference) cooling rates of 5° C./sec or less cause unpredictable necrosis, and one needs to achieve cooling rates in excess of 10° C./sec to achieve consistent tissue necrosis.

Nir Merry, et al. (U.S. Pat. No. 4,946,460) uses very slow cooling rates (few degrees/minutes) which cause partial necrosis. Merry's devices are aimed at the eradication of malignancies, and he tries to destroy the vasculature permeating the target lesion. The malignancy is destroyed, when its blood vessels are destroyed, due to blood supply deprivation. Merry, et al. states that at slow cooling rates ice forms in the blood vessels, rejecting solutes (mostly salts) to the yet unfrozen blood and the freezing temperature of the concentrated saline drops. Water from neighboring unfrozen tissues migrates through the blood vessels' membranes (due to the high osmotic pressure in the now concentrated solution) until the expansion of these vessels leads to their destruction. Yet other researchers (Marchenko, et al. U.S. Pat. No. 4,528,979) first freeze the target tissues with a cryodestructor which achieves only partial necrosis, and then applies an ultrasonic beam to the frozen tissue, which completes the tissue cells' destruction.

Most current cryosurgical probes cool using very high pressure gas which undergoes expansion through a Joule-Thomson valve. Such probes require walls that can withstand the high gas pressures and such thick walls make the devices bulky and impossible to use in a number of procedures. When a combination of the Joule-Thomson effect, together with the use of evaporation cooling is used, similarly high gas pressures are used and the devices are also bulky. All these above-mentioned cryogenic devices use relatively thick walls, so that the probes are relatively inflexible. When evaporative cooling with liquid nitrogen is used (for instance, in Marchenko's devices) a flexible catheter is not possible as elastic materials become embrittled at the applied cryogenic temperatures. There are a number of procedures, particularly treatment of severe arrythmia, where the availability of a flexible freeze ablation catheter allows for non-surgical intervention. This cannot be achieved with cryosurgical probes of the prior art due to their inflexibility.

In addition, it is often desired to keep the tip of the cryosurgical probe at ambient temperature, or at least above freezing, until actual cryogenic necrosis is desired. This is difficult because the cooling rates reached are often too slow to achieve the desired reproducible necrosis. To overcome this shortcoming, Mitchiner U.S. Pat. No. 4,275,734 controls the temperature of the cryogenic gas supply cylinder and raises its temperature somewhat above ambient. As a result, the pressure of the cryogenic gases is maintained within the range of 600 to 850 psi., which higher than in most cryosurgical devices. Such high pressures require probes that can withstand these pressures, and systems to operate these probes that are costly and difficult to operate.

In general, the prior art cryosurgical devices could not provide for flexible, catheter-like cryogenic probes that are able to be directed to specific pathological locales, either through the arterial system or through a tubular conduit inserted in small incisions.

SUMMARY OF THE INVENTION

In accordance with the present invention, there is provided a probe or catheter used to deaden tissue cells at a small selected location, for example, to destroy arrhytmogenic foci in cardiac procedures. The probe has a head portion and an elongated tubular portion leading to the head portion. The tubular portion is a conduit, in one embodiment, from a source of cooled liquid to the head portion and a return from the head portion. Preferably the tubular portion is a coaxial member having an inner bore through an inner tube (inner lumen), an outer tube (outer lumen), and a liquid flow path between the inner and outer tubes.

The flow of cooled liquid to the head portion rapidly cools the tissue cells proximate the head portion to below freezing, in the range of about −10° C. to −50° C., without cooling the cells below about −50° C. While the tissue cells are supercooled, they are subjected to ultrasonic cavitation energy which is within a critical range of power so as to cause nucleation of ice within the cells. Preferably the ultrasonic energy is from a transducer at the probe head portion; however, in appropriate situations the ultrasonic energy may be applied non-invasively by a transducer applied to the skin of the patient.

The probe is less likely to cause damage to cells beyond those sought to be killed due to the limited temperature and rate of its supercooling, i.e., above −50° C. and due to the low power of its ultrasonic energy, which is considerably below the ultrasonic power required to rupture cells.

OBJECTIVES OF THE INVENTION

It is a primary object of the instant invention to provide improved medical surgical methods and devices which avoid the need for a cryogenic probe using high gas pressure.

It is another object of the present invention to provide for intra-cellular nucleation in the target tissues at temperatures which are close to the melting temperature of physiological tissues and thus avoid the need for very rapid supercooling of the tissues.

It is yet another object of the present invention to provide surgical implements for the freeze-deadening of tissue which are flexible enough to be used as catheters in cardiac, laproscopical and endoscopical procedures.

It is yet another object of the instant invention to provide for a freeze-deadening catheter for cardiac procedures, capable of first lowering the temperature of the ablation target tissue to determine and ascertain the correctness of the target location followed by the freezing and deadening of the target tissue cells.

BRIEF DESCRIPTION OF THE DRAWINGS

Other objectives of the present invention will be apparent from the following detailed description taken in conjunction with the accompanying drawings, in which:

FIGS. 2A-2C and 2E are side cross-sectional views showing details of the tip of three preferred embodiments of the instant invention; and FIGS. 2B and 2C are cross-sectional views taken along lines a—a of FIG. 2A and b—b of FIG. 2C respectively;

FIGS. 3B-3C show the details of the tip for two additional preferred embodiments of the instant invention, in which FIGS. 2A and 2B are side cross-sectional views and FIG. 2B is a cross-sectional view taken along line c—c of FIG. 3A:

FIG. 4 shows an enlarged cross-sectional view through the double lumen of the catheter of the present invention;

FIGS. 5A and 5B are cross-sectional views which describe schematically the extent of necrosis inflicted by different catheter tips;

DETAILED DESCRIPTION

In the instant invention, we provide a method and device for causing tissue necrosis (deadening of tissue cells) without the extremely rapid cooling required in the prior art and as a result without the need for high pressure cryogenic gases. This permits the use of flexible catheters and fine probes.

The process by which a liquid when cooled through its melting point crystallizes (solidification) involves two distinct mechanisms, crystal nucleation and crystal growth. The driving force for solidification is the difference in free energy between the liquid and solid phases at a given temperature (mostly the heat of fusion). To clarify the concepts disclosed herein, we will use the following definitions, which are well accepted in physics.

The "melting point" or temperature of tissue is the temperature at which the solidified tissue mass is converted to liquid while the temperature is being raised. In biological tissues, especially human tissue cells, this temperature depends on the tissues' composition and due to the complex chemical and physical nature of biological tissue, is not necessarily well determined. A good working assumption is that the range is between $-2°$ C. and $-5°$ C.

Given an infinite time, and at least one solid nucleating site, the "freezing point", (temperature at which liquid is converted to solid as tissue temperature is lowered) is equal to the melting point. In practice, the freezing point is always somewhat below the melting point. Tissue which has not solidified although its temperature has been lowered below the melting point is termed "supercooled tissue". In biological systems the freezing process is further complicated by the heterogeeous nature of the tissues and the existance of semipermeable cellular membranes. This causes the freezing process to be the result of a number of competing processes, including the rate of ice nucleation, crystal growth rate, the rate of removal of the heat of fusion, solute rejection rate from forming crystals and the diffusion rate of solvent and solute (water and mostly electrolytes respectively) through intercellular membranes.

A condition for triggering the phase transition between the liquid and the solid phases is the formation of embryonic nuclei in the liquid. This requires the establishment of surfaces between the liquid and the newly formed nuclei, a process which increases the free energy of the system by the surface energy associated with the formation of such surfaces. Since the surface energy of each embryonic nucleus increases with the square of its radius and the difference in free energy between its solid state and its liquid state increases with the cube (volume) of its radius, very small nuclei are not thermodynamically stable because they tend to increase the total energy of the system.

Once a critical size of such an embryonic nucleus has been reached, however, the energy gained from the heat of fusion is larger than the energy required to increase the nucleus' surface, and the nucleus' further growth, lowers the free energy of the system. Such nuclei are therefore thermodynamically favored, they are stable and continue to grow until the liquid phase is converted to the crystalline solid phase. The minimal radius of a stable embryonic nucleus is termed the "critical radius", and is the radius at which the gain in free energy between the two states equals the energy required to form the new surface. Subcritical embryonic nuclei are formed and redisolved through thermodynamic fluctuations in supercooled fluids, but only these embryonic nuclei that have reached the critical radius continue to grow and are thus thermodynamically stable.

There is a distinction between homogeneous and heterogeneous nucleation in solidifying liquids. Homogeneous nucleation rates depend only on the thermodynamic properties of the liquid, heterogeneous nucleation occurs on pre-existing surfaces (usually undisolved impurities or external solid surfaces) whose presence obviates the need to supply the energy for forming the embryonic nucleus' surface, or at least, drastically reduces the surface formation energy, and thus the critical radius.

For any liquid one can, in principle, define a homogeneous solidification temperature, which would be the lowest possible (equilibrium) temperature at which homogenous nucleation occurs. Due to the impossibility of maintaining supercooled systems free of any impurities, there are always some uncertainties in the determination of this temperature. For water, however, a temperature of $-40°$ C. is accepted as the homogeneous freezing temperature. Freezing of water at temperatures higher than the homogeneous freezing temperature requires the presence of pre-existing nucleating surfaces.

While the mechanism of freezing biological cellular structure (tissue cells) is far from being understood, it is possible to provide a qualitative explanation of the process. When physiological tissue is cooled slowly below its melting point, about $-2°$ C. to $-5°$ C., the liquid-filled interstices between the cells provide ideal nucleation sites for ice. Within the cells the homogeneous nucleation temperature is probably lower than $-20°$ C. On cooling to below $-2°$ C. the interstitial ice grows (between the cells) while the cellular matter (within the cells) is supercooled. As the interstitial ice grows, it absorbs water from the surrounding cells, causing dehydration of these cells. When the temperature of the intracellular matter finally reaches the homogeneous nucleation temperature (about $-20°$ C.) sufficient dehydration has occurred that residual intracellular freezing does not result in membrane rupture, and thus necrosis (cell deadening) is absent or incomplete. This process is the basis for cryogenic preservation of physiological tissues, which is always achieved at relatively slow cooling rates.

Variants on this process, for instance, in the presence of major vascular tissue within the target tissues, is described by Merry, et al. (see above). In this case the process involves very slow cooling, for example under some cooling regimes, a gestation period of 5 minutes near 0° C. is required. Such slow cooling allows for relatively slow process of saline rejection from the forming ice to occur. This causes an osmotic pressure rise in the vascular vessels. That pressure rise, in turn, causes water to migrate into the vasculature and cause their rupture. The rate controlling processes in this technique are saline rejection from the forming ice and water diffusion through the relatively thick membranes of the vasculature. Both processes are extremely slow and as a result the procedure is not very practical. Furthermore, this technique can be used only where the tissue is highly permeated with vasculature.

The processes of nucleation and crystal growth compete with each other. When cooling rates are slow, mostly interstitial nucleation and growth occurs due to the lack of nuclei within the cell. When the cooling rate is rapid and the inner part of the cell reaches temperatures below $-20°$ C. before interstitial ice has had the opportunity to grow, intra-cellular nucleation occurs prior to dehydration, and further growth of these nuclei causes membrane rupture (cell necrosis). In some surgical procedures complete cell deadening (necrosis) is desired and may be incomplete due to the slow cooling of the cells.

In experiments with water droplets (D. R. Worsnop, et al. "Heterogeneous Reaction Kinetics of Importance to Stratospheric Chemistry" Aerodyne Research Report No. ARI-RR-613 (1988)) the droplets were 200 microns in diameter, supercooled and frozen heterogeneously within 20 msec. This indicates that once nucleation has been achieved, the growth rate of the nucleli within the droplets (which are much larger than the target tissue cells) is extremely rapid, of the order of 10 msec or less. While we know of no comparative measurements in biological tissues, the growth rate within a cell is probably comparable to the growth rate observed in water. However, when the rate controlling process for ice growth is the diffusion of water molecules through cell membranes (interstitial nucleation followed by surrounding cells dehydration), the growth rate of interstitial ice is likely much slower than the growth rate of intracellular ice. One would deduct, therefore, that in slowly supercooled biological tissues, the artificial provisions of intracellular nucleation sites would result in essentially instantaneous freezing of the intracellular matter and minimization of interstitial freezing.

The instant invention avoids extremely rapid cooling and does not use high pressure cryogenic fluids, i.e., high pressure gas. The present invention artificially provides heterogeneous nucleation of ice throughout the tissues and forces initiation of ice growth within the cells and interstitially. Once nucleation within the cells has occurred, the intracellular ice growth is faster than intercellular ice growth due to growth limiting water diffusion through the membranes in the latter process. Thus, prefreezing dehydration of intracellular matter is avoided and the expansion of ice within the cells near the freezing temperature causes cell rupture and the desired necrosis. The desired artificial nucleation surfaces are provided by ultrasonic cavitation. Supercooling down to $-15°$ C., is achieved by a low pressure circulating coolant, i.e., low pressure liquid. The cells, as they are being super cooled are subjected to ultrasonic cavitation (weak cavitation) which provides for rapid intra-cellular freezing of the desired tissue cells and the rupture of their membranes (necrosis).

Figure 1:
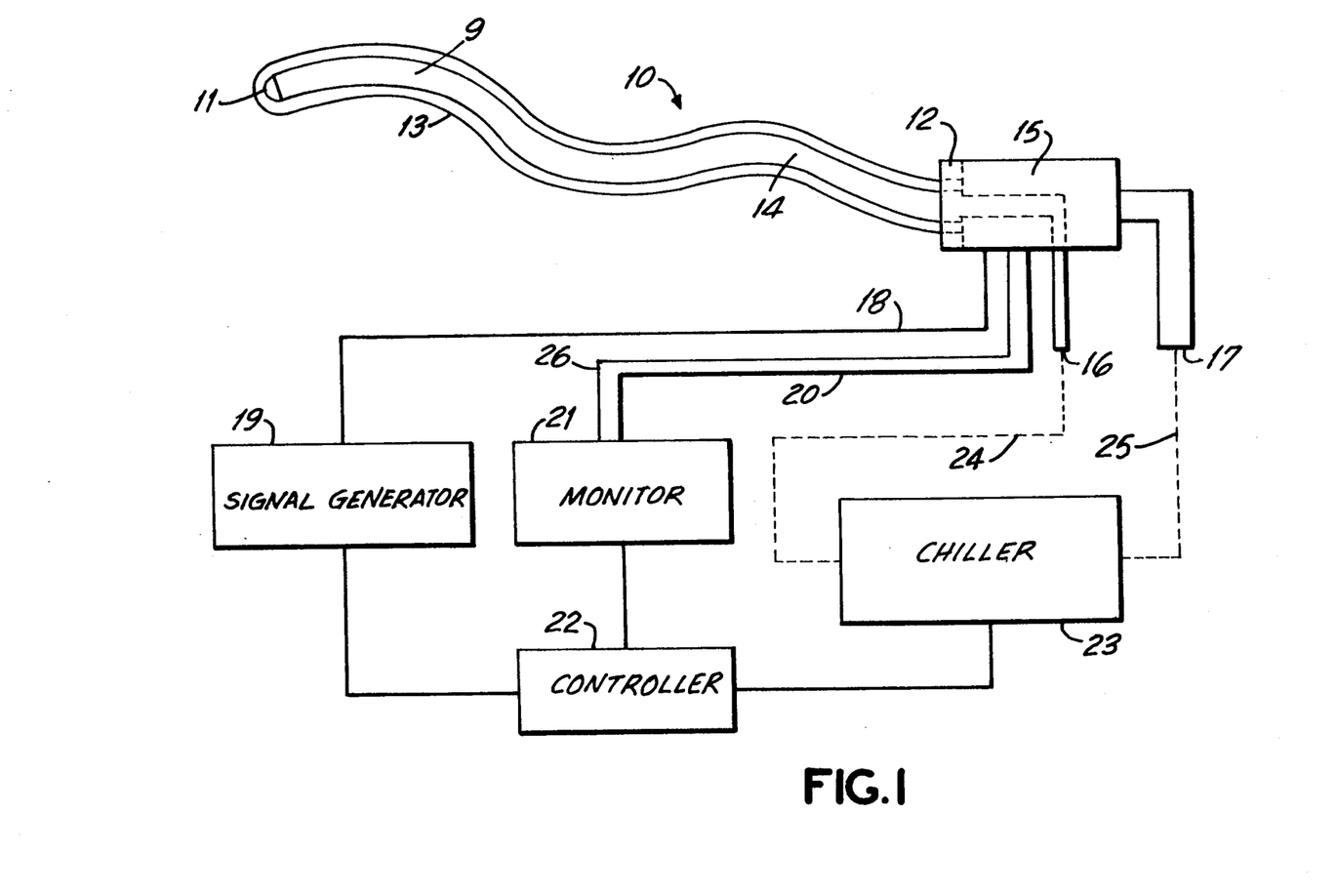
FIG. 1 is a side view of the catheter or probe of the instant invention and a block diagram of its associated support devices.

In FIG. 1, a catheter 10 is constructed from flexible tubing, extruded for instance, from a silicone polymer (from Petrach Systems, Bristol, Pa.) or from "Peek" a polyetheretherketone (T. M. Uptech, Oak Harbor, Wash.) capable of keeping its flexibility to $-30°$ C. The catheter is terminated at its distal end (inner end) with a tip 11 (head portion). The details of a number of embodiments of this tip are given in FIGS. 2 and 3. The catheter body portion 9 consists of two concentric tubular structures (double lumen structure), an external lumen 13 and an internal lumen 14, each of which is an elongated flexible tube. A cross section through the double lumen is shown in FIG. 4. The two lumens are not necessarily made of the same materials. The external lumen withstands fluid pressure in the range of about 150 to about 200 psi but need not be flexible to $-30°$ C., since the external lumen 13 is always at temperatures above freezing. The internal lumen 14, on the other hand is made of a material capable of keeping its flexibility to $-30°$ C. but is not required to withstand the same high pressures as the outer lumen. At the proximal end (outer end) the catheter 10 body portion 9 is terminated with a plug-like connector 12 that allows easy insertion to the fixture 15. Fixture 15 can have any of many possible shapes including without limitations, a cylinder, a handle or a paralleliped.

The fixture 15 is hollow and has an entry portion 16 connectable to the inner lumen 14 of the catheter 10 on one end and to a liquid containable tube 24. A circulating chilled fluid is chilled in an external chiller 23 connected to the tube 24. The flow direction of the chilled fluid is toward the distal end of the catheter through the inner lumen 14 of the catheter 10. The fluid first cools the target tissues and then carries heat of fusion from the tissue. The return of the liquid to the chiller is in the tubular space between the inner and outer tubes of the catheter. The outgoing cooling fluid flows through the hollow of the fixture 15 to an exit portion 17 and through tube 25 to the chiller 23 for cooling and recirculation. The connection of the fixture 15 with the plug-like termination of the catheter is self sealing so that, when the plug 12 is inserted in the fixture 15, the fluids can flow in their respective paths, but when the plug is disconnected, the fluid cannot escape. This can be achieved either by valves on the respective tubes or by spring loaded seals. The fluid conduits 24 and 25 as well as the electrical lead pairs 18, 20, and 26 (described below), are preferably consolidated into a single multi-element "cable" ported to the fixture 15.

A piezoelectric transducer 11 (available from Nutran, Everet Wash.) is positioned at the distal end of the catheter 10. Preferably the central frequency of the ultrasound beam produced by transducer 11 is at about 150 MHz, with the velocity of sound somewhat in excess of 1500 m/sec, that frequency provides a wavelength in the range of 30 to 50 microns, assuring good intracellular cavitation distribution. The preferred range is from about 7.5 MHz to about 500 MHz with the most preferred range being from about 30 MHz to about 200 MHz. The lower frequencies, down to 7.5 MHz may suffice as transient pressure gradients generated within the cells are often sufficient to initiate nucleation. The preferred, power density range is from about 10 to about 200 milliwatts $cm^2$, depending on the specific tip design. These relatively low power ratings are sufficient to cause the required microcavitation but not sufficiently high to cause cell lysis via large cavity collapse and cell implosion. Such a low power rating also assures a minimal thermal loading on the heat exchanging liquid.

FIG. 2 shows three preferred embodiments of the tip 11 denoted respectively 30, 40 and 50. In FIG. 2A, tip 30 has a piezoelectric transducer 31, with a generally cylindrical shape. The active part of the transducer is a very thin layer on the face of the transducer, between 0.01 to 0.5 mm and this thickness depends on the desired center frequency of the ultrasound. This active layer is only on the distal tip of the transducer and generally not shown. In FIG. 3C an example is demonstrated. A cross section through the plane a—a of the tip 30 is shown in FIG. 2B. The element 31 has a bore 32 in its center. The transducer 31 fits within the external lumen 33 of the catheter (lumen 13 of FIG. 1) and the internal lumen 34 (lumen 14 of FIG. 1) fits within the bore 32. On the outer envelope of the transducer 31, a multiplicity of cooling channels 35 allow for the cooling fluid to pass back to the tubular space 135 between the two lumens. Two conductive wires 36 and 37 supply the power actuating the transducer 11.

The piezoelectric crystal transducer 31 is traversed by a fluid which is preferably cooled to about $-10°$ C. to $-15°$ C., but could be cooled as low as $-30°$ C. The wires 36 and 37 from the piezoelectric transducer 31 are within the space 135 between the two lumens and end in the plug-like connector 12 (FIG. 1). Referring back to FIG. 1, in the plug-like connector 12 contact is made to mating leads in the fixture 15 to connect these wires 36 and 37 to line 18 (a dual conductor line). Line 18 provides the power from a signal generator 19 to the piezoelectric transducer. A similar pair of wires (38 in FIG. 2A) connects a thermistor 136 (Fenwal Electronics, Milford, Mass.) from the tip of the catheter to line 20, which is monitored by a high sensitivity voltmeter 21, to determine the temperature of the piezoelectric transducer 31 and thus of the cooled tissues. The transducer 31 leads are simultaneously used to detect electrical activities in the tissues to be ablated, prior to the application of an activating signal. A third pair of wires 26 in FIG. 1 are electrodes to determine the electrical activity of the region being cooled prior to the activation of the ultrasonic transducer 31. An electronic controller 22, for example a PC (Personal Computer) digital computer system, coordinates the operation of the system according to a preset schedule.

In the preferred embodiments of this invention, the cooling fluid is a dielectric liquid, which carries the heat of fusion as well as the heat generated by the transducer away from the cold tip (head portion) without shorting the transducer 11. A preferred liquid is trymethylsiloxy terminated polydimethylsiloxane, for instance, "PS037" (T. M. of Petrarch Systems, Bristol Pa.). That polydimethylsiloxane has an electrical resistivity in excess of $10^{10}$ ohm-cm at $-30°$ C. and a breakdown voltage of about 4,000 volt/mm. The specific heat is about 0.37 cal/gm and the density about 0.9 gm/cc.

Figure 2A:
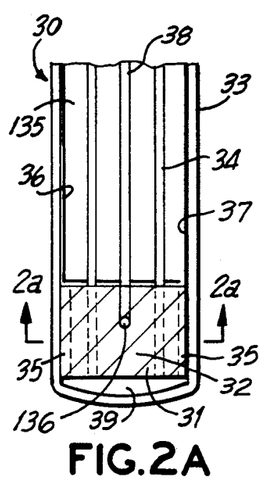
Figure 2B:
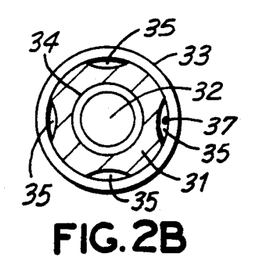

In the embodiment shown in FIGS. 2A and 2B, the ultrasonic energy is transmitted through a small pocket 39 of the heat transfer liquid and the external lumen tips. In this configuration a portion of the ultrasonic beam is reflected back from the lumen due to impedance mismatch at the various interfaces introduced and some attenuation (absorption) in the lumen occurs as well. The advantage of this configuration is the excellent thermal transfer properties achieved by the presence of the moving fluid at the external lumen interface, i.e., at pocket 39.

Figure 2C:
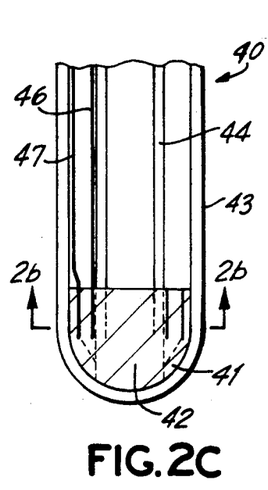
Figure 2D:
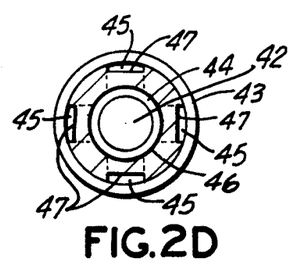

As explained below, it is sometimes desired to have a spherical tip, of the type shown in FIGS. 2C and 2D in which FIG. 2D is a cross section through the plane b—b of FIG. 2C. The distal end of the tip 40 is spherical and the transducer 41 is terminated with a hemisphere nested within the distal end of the external lumen 43. As mentioned above, only the outer hemispherical layer is the active element, see for example, FIG. 3C. The transducer 41 is traversed axially with a bore 42 to allow irrigation of both sides of the transducer. The inner lumen 44 is nested with the bore 42. The face and side of transducer 41 have channels 45 to allow the liquid movement and the external lumen 43 serves as a transmitting medium to the tissue. Only a limited area of the transducer's distal face (through the channels 45) is in contact with the cooling liquid. The wires 46 and 47 powering the transducer are concentric, the inner wire 46 is positioned in the bore 42 and the outer wire 47 in each of the vertical segments of the channels 45.

Figure 2E:
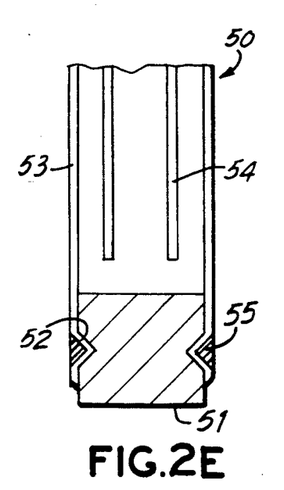

In another preferred embodiment, shown in FIG. 2E the external lumen 53 is terminated with the transducer 51 and heat is conducted through the transducer 51. Here the tip 50 is terminated with a solid cylindrical transducer 51, having a fastening notch 52 on which the external lumen 53 is fastened with a retaining ring 55. The inner lumen 54 is terminated a small distance from inner surface of the transducer 51 allowing cooling fluid to remove heat of fusion as well as heat generated within the transducer from the back end of the transducer. Electrodes and thermistors are placed as described earlier. This tip optimizes the transfer of ultrasonic energy to the tissues but is somewhat less efficient from the thermal transfer point of view.

When the instant invention is used as an arterial catheter it is usually desired to keep the external diameter of the catheter under 3 mm, and preferably in the range of 2 to 2.5 mm. The distal end of the catheter, however, can have a larger diameter this enabling the necrosis of larger areas. Such tips are described in FIGS. 3A–3C.

Figure 3A:
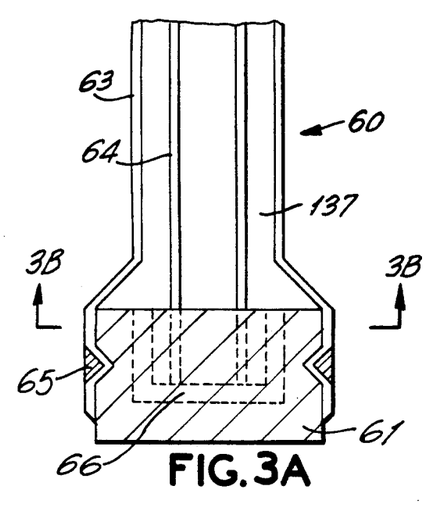
Figures 3B, 4, 5A, 5B:
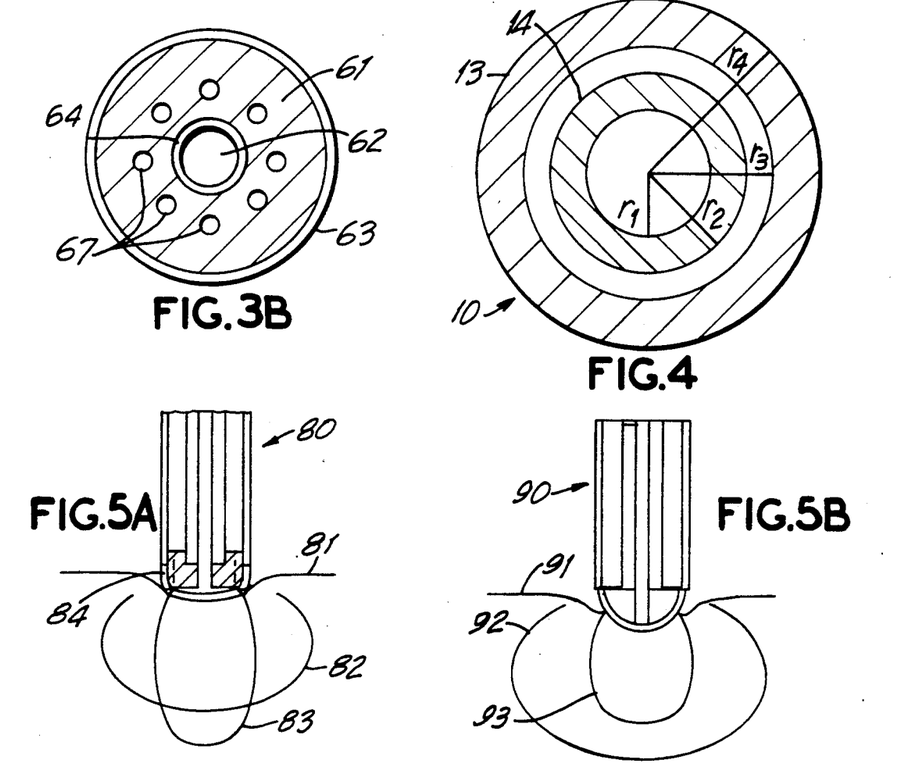
Figure 3C:
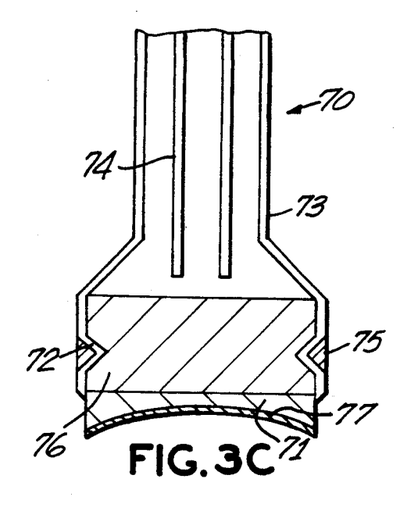

In FIG. 3A a tip 60 terminates with a transducer 61, in a fashion as described for the tip in FIG. 2E. The transducer 61 is partially perforated with a cylindrical bore 62 in which the inner lumen 64 is inserted. The return path for the cooling fluid is provided by an undercut 66 connected to a multiplicity of holes 67 which direct the cooling fluid to the space 137 between the inner lumen 64 and the outer lumen 63. Other aspects of the tip are as described in connection to the embodiment of FIG. 2A. FIG. 3B represents a cross section through the plane c—c of FIG. 3A. This design has the advantage of high transducer efficiency, due to the direct coupling with the target tissue, and optimizes heat transfer as well.

As shown in FIG. 3C another wide tip embodiment uses an unperforated concave transducer. Here the tip 70 is terminated with a transducer 71 cemented on a thermally conductive back 76 (for instance, cooper). The active element of the transducer 71, is the thin layer 77. This active element can be made from a piezoelectric ceramic like lead zirconium titanate (PLZT), or an organic piezoelectric substance such as polyvynilidene fluoride (PVDF). The outer lumen 73 is fastened on a notch 72 (on the conductive backing 76) with a fastening ring 75. The inner lumen 74 directs the flow of the cooling fluid onto the back end of the conductive element 76 and thus that flow withdraws the heat of fusion and the heat generated within the transducer. This design allows for a focused ultrasonic beam, high efficiency of transfer of the ultrasonic energy to the tissues, and good heat transfer properties.

It is important to cool the target tissues rapidly through the melting point to avoid intercellular ice growth prior to achieving intracellular heterogeneous nucleation. In order to cool rapidly (in one second) tissues having the dimensions 1 cm × 1 cm × 0.5 cm from 37° C. to −3° C., including withdrawal of the tissues' heat of fusion, one must withdraw 60 calories in a second (or about 240 Watt cooling rate). This value presents an upper limit on the requirement of the device. With the silicon fluid mentioned above at −30° C., a flow rate of 10 cc/sec or 600 ml/min is sufficient (the specific heat of the preferred liquid silicone compound is about 0.4 cal/gm/°C.). In practice, because the rate controlling process of interstitial ice growth is water molecules diffusion through cell's membrances, the time allowed (to avoid interstitial ice growth) is closer to the range of 5 to 10 seconds, and the volume affected is smaller. Nevertheless, when designing an actual catheter, faster cooling capabilities should be provided than the minimum required.

Most of the heat load on the heat transfer fluid is due to the heat of fusion exuded from the ablated tissues. When cooling to the tissues' melting point, without freezing, a flow rate of the cooling liquid in the range of about 100 to 150 ml/min is sufficient to lower the target tissue's temperature and withdraw heat conducted through those tissues from surrounding warmer tissues.

To demonstrate the structure and typical dimensions of the double lumen catheter, FIG. 4 shows a cross section through the double lumen catheter body portion, i.e., at a place removed from the tip. The four radii denoted $r_1$, $r_2$, $r_3$ and $r_4$, are respectively the inner diameter of the inner lumen 14, the outer diameter of the inner lumen 14, the inner diameter of the outer lumen 13, and the outer diameter of the outer lumen 13. The specific dimensions depend on the desired application. Thus for a cardiac catheter which is typically inserted through the femoral artery, an external diameter of between 2 to 3 mm is desired (between 6 to 9 french). The specific choice of the tube sizes also depends on the pressure available on the cooling liquid and the flow rate desired. For freezing of cardiac tissues, as in the treatment of severe tachycardia, it is desired to ablate tissues in an area about 3 to 5 mm in diameter and about 3 to 5 mm thick. For such a result, a flow rate of about 300 ml/min of "PS037", chilled to −20° C., is sufficient to cool and remove the heat of fusion of the target tissue. A preferred dual lumen catheter of 80 mils (2 mm) OD has the following dimensions (see FIG. 4):

$$r_1 = 22 \text{ mils}, r_2 = 26 \text{ mils}, r_3 = 34 \text{ mils and } r_4 = 40 \text{ mils},$$

That cathater is used with a pressure of between 70 to 140 psi to achieve the desired flow. The higher range of pressures allow for removal of the heat generated by the transducer. The inner lumen is preferably of a silicon polymer and the outer lumen preferably is made of "Peek" or aother flexible polymer, such as polyurethane.

The pressure on the cooling fluid can be further reduced by using a somewhat larger cross section catheter. For instance in a dual lumen catheter having the following dimensions (2.5 mm OD):

$$r_1 = 30 \text{ mils}, r_2 = 34 \text{ mils}, r_3 = 44 \text{ mils and } r_4 = 50 \text{ mils}$$

the pressure range can be lowered to about 38 to 76 psi to achieve the same flow rate of about 300 ml/min, or alternately the flow rate and pressure can be increased.

For other applications, for example in rigid freezing probes for stereotaxis neurosurgery, wider or thinner probes can be designed following the design principles as delineated above. The term "catheter" as used in the claims covers both a flexible catheter and a stiff (rigid) probe.

The operation of the device is set forth below in which the method for a typical cardiac ablation is described. First the catheter is inserted through the appropriate venue (for instance the femoral or carotid arteries) so that its distal tip is in contact with the tissue to be ablated (deadened). The pick up electrodes monitor the electrical activity of the target tissue (in other words an intracardiac electrocardiogram is taken) and assure the correct position of the tip. The tip's position is preferably monitored with an appropriate X-ray device and manipulated by, for instance, a guide wire or manual manipulation as, is commonly practiced in the art. Until the correct position is attained, the fluid within both lumen of the catheter are at ambient temperature and the recirculator 23 inactive. Once the catheter tip is at the right location, next to the tissue to be ablated, the recirculating pump is turned on and forces the heat exchanging fluid from the recirculating chilled reservoir 23 to flow through the inner lumen of the catheter and to chill the tissue in contact with the catheter's tip. Initially a flow rate of only about 100 ml/min is used. This chills the target tissues to a temperature range of about −1° C. to 5° C. which results in a sharp decrease or complete cessation of electrical activity. By monitoring the intracardiac electrocardiogram, the surgeon is assured that he has indeed located the arrhytmia focus. The pressure of the heat exchanging fluid is now increased to provide a flow rate of about 300 ml/min and as a result supercooling of the target arrhythmia focus occurs.

As supercooling is achieved by the moving chilled liquid, the ultrasonic transducer is activated for a short time causing nuclei in the tissue cells and the supercooled tissue freezes. In other words, as the target tissues are cooled below their melting points, the energy required to form nuclei surfaces is provided ultrasonically by cavitation within the cells and intracellular heterogeneous nucleation occurs, followed by reproducible and locally well defined necrosis. To prevent initiation of freezing intercellularly, the transducer is preferably activated simultaneously with the increase in chilled fluid flow. The proper sequencing of the various activities involved in the operation of the system, including increasing the pressure on the heat exchanging fluid during preablation cooling, further pressure increase when ablation is started and the simultaneous (or slightly delayed) actuation of the transducer is provided by the controller 22 (FIG. 1). The pressure on the heat exchanging fluid and thus its flow rate, are controlled to achieve a specific temperature at the target tissues by incorporating in the control strategy of the controller 22 the measured temperature of the tip.

One of the advantages of the instant invention is that it provides a high degree of flexibility. FIG. 5 schematically demonstrates some of the control parameters available to the operator of the freeze ablation catheter of the instant invention. In FIG. 5A a flat tip 80 is pressed against tissue 81. Tip 80 is of the type described in FIG. 2A except that the distal end 84 is metallic to further improve both thermal and acoustical coupling of the tip to the target tissues. Within a short period (about one to three seconds after the initiation of the chilled fluid flow) a thermal gradient is established within the affected tissue. The line 82 depicts a typical isothermal surface (axially symmetric) within the affected tissue. Lower temperatures are achieved within 82 and higher temperatures outside 82. The isothermal 82 is at $-5°$ C. to $-10°$ C. This temperature range provides sufficient supercooling to initiate intracellular freezing, providing nucleating surfaces are present.

The energy density of the ultrasonic beam in the tissues is a strong function of the transducer geometry and construction. In general this energy density will decline as the distance from the emitting surface increases. This is due to attenuation within the tissue as well as to "spreading" of the beam. While the exact mathematical expression describing the decrease in beam energy density with position is difficult to obtain, the decrease is usually at least quadratic with the distance from the ultrasonic transducer's emitting surface, when this surface is spherical. The line 83 depicts the ultrasonic beam equienergetical surface (axially symmetric) sufficient to cause cavitation in the tissues. Due to relatively strong attenuation the beam's energy outside the surface 83 is not sufficient to cause nucleation and is more than sufficient to cause nucleation within the surface 83. When the ultrasonic transducer is activated, within a space enclosed by the line 83 cavitation nucleation occurs and because the temperature within this space is sufficiently low, rapid tissue freezing occurs. When the cells freeze they expand in volume which causes their membranes to rupture and thus necrosis. Such necrosis occurs only within the common space enclosed by the surface 82 and 83. Since the energy of the ultrasonic beam within the surface 83 is far below that required to cause cell lysis, the space outside the surface 82 but within 83 does not undergo necrosis. When very high energy ultrasonic beams are employed, large cavities can be formed within the cells and their instantaneous implosion can cause cell lysis. In the practice of this invention weak cavitation, and sometimes only pressure gradients are sufficient to cause intracellular ice nucleation. The beam's energy densities used in the practice of the instant invention are between one to three orders of magnitude lower than traditionally used for cell lysis.

FIG. 5B shows a spherical tip 90 (of the type described in FIG. 2C), pressed slightly on the target tissue 91 in which the cooling fluid flows at the same rate as in the tip 80, but due to better heat transfer geometry in tip 90, the isotherm 92 is somewhat larger than the isotherm 82 (FIG. 5A). Conversely, the effective range of the ultrasonic beam is somewhat narrowed as depicted by the surface 93, and as a result only the tissue within both surfaces 92 and 83 is rapidly frozen.

For any given tip configuration, the operator can control the extent, within some limits, of the isothermal surfaces 82 or 92 by increasing or decreasing the rate of flow of the heat exchanging fluid. Similarly, by increasing or decreasing the power to the transducer, the size of the surfaces 83 and 93 can be modified. These control parameters allow therefore for freeze ablation device with a high degree of versatility.

Since deep supercooling is avoided, the formation of an ice ball at the distal end of the catheter is usually avoided. Furthermore, the thermal mass of the tip is under 5 calories, thus all that is required to release the tip from the necrosed tissue, is stopping the flow of the recirculating coolant. This causes rapid reheating of the tip (through conduction from the surrounding tissue and the circulating blood) above the tissue's melting point so that the tip may be pulled away from the necrosed tissue without injury to the surrounding live tissue.

Figure 6A:
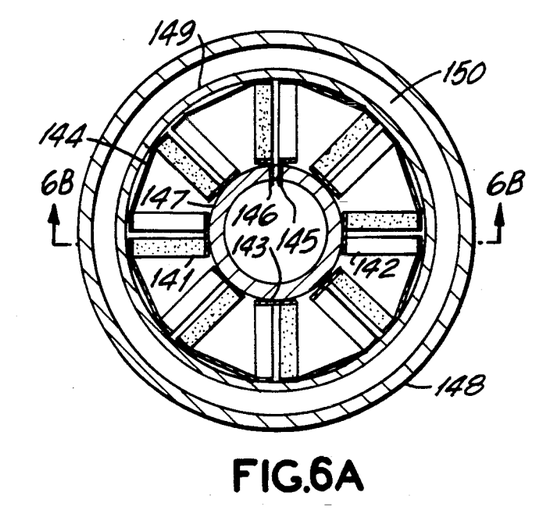
FIG. 6A is an end cross-section and FIG. 6B is a side cross-section of a catheter tip utilizing a thermocell device.

The catheters and probes of the present invention may use a thermocouple cooling device within the catheter for freezing the tissue cells, since extremely low temperatures are not required. FIG. 6A shows a small thermoelectric cell whose preferred dimensions are 2 mm to 3.5 mm (and up to 25 mm long) in diameter and which delivers between 3 watts $-25$ watts of cooling. The preferred structure of the thermoelectric cell is the tubular cell shown in FIG. 6, which is described below and further details of which are described in the inventor's copending U.S. patent application Ser. No. 07/626,986, filed Dec. 13, 1990, incorporated by reference herein (copies available from the Patent Office or the inventor). The thermoelectric cell is at the distal end (tip portion of the catheter).

Figure 6B:
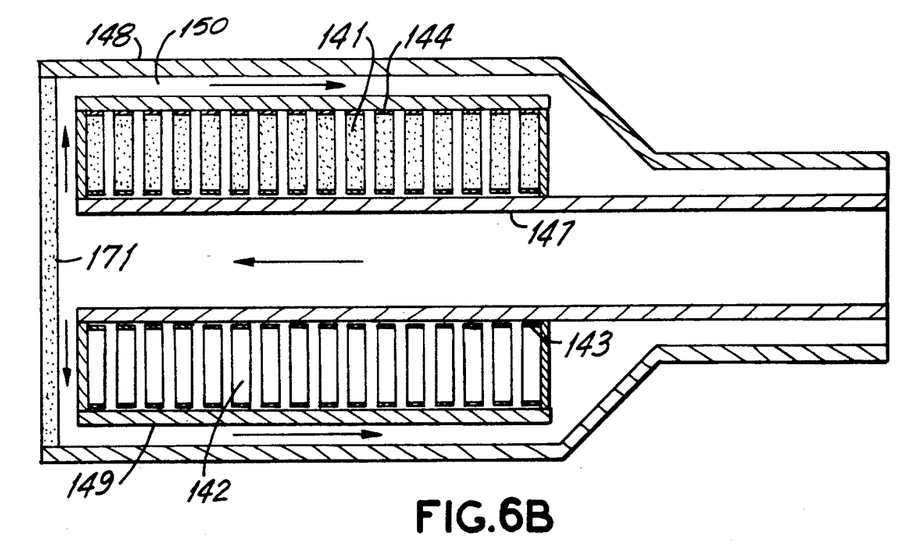

FIGS. 6A and 6B show cross-sections of the preferred thermoelectric cell. The thermocouple elements are arranged radially. The elements 141 are p-type thermoelectric semiconductors and the elements 142 are n-type thermoelectric semiconductors for instance p and n type bismuth telluride. At the inner base, the elements are connected with an electrical conductor 143 and at the top they are connected with a conductor 144 in such a manner that all the elements are connected in series and powered through the leads 145 and 146 respectively. A number of these ring like thermoelectric assemblies are mounted side by side between the inner tube 147 and the outer tube 148, as shown in FIG. 6B. A bracing structure 149, also serves to seal the thermoelectric cooler from the heat exchanging fluid flowing through the device. The leads 145, 146 of the various rings are connected in parallel, to wires which extend through the catheter to its proximal end. When a DC current is passed through the leads and the thermocouples, a thermal gradient is established on each of the cells' rings between the center tube 147 and the bracing structure 149.

Heat is pumped from the center tube 147 of the cylinder to the space 150. By reversing the current's direction, the thermal gradient may be reversed and the direction of heat transport is also reversed. This reversal can be used at the end of the procedure to help thaw the frozen zone.

The heat exchange liquid is any low melting point (under −25° C.) liquid which is externally precooled to between 0° C. to about −10° C. The liquid is pumped through the tube 147 where it is further cooled by the thermoelectric cell to about −25° C. The liquid comes in contact with the ultrasonic transducer 171 and withdraws heat from the tissues.

The transducer 171 is an ultrasonic transducer connected to wire leads (not shown) which are within the path 150 (space between the tube 148 and the thermoelectric cell's bracing structure 149). When reversible anesthesias is desired, the thermoelectric cell is operated at a low power, and once determination of the appropriate site has been achieved, the thermoelectric cell's power is increased, cooling the heat exchanging liquid at the distal end to about −25° C. The liquid returns by a liquid path 150 within the outer tube 148 of the catheter (the space between the cell's bracing structure 149 and the outer tube 148). The liquid pumped through path 150 removes with it the heat taken from the inner hollow liquid tube 147, the transducer 171, and the frozen tissues and the energy input of the thermoelectric cell. This warms up the liquid to a temperature quite close to the body temperature, and possibly higher, which prevents freezing of the catheter to the arteries. One of the advantages of this thermoelectric configuration is that the quantity of heat withdrawn per unit current is highest at the cold tip. The tip is also at the exact location required for maximum heat removal efficiency. The maximum heat uptake due to the exudation of heat of fusion by the tissue being frozen is at the tip.

Figure 7:
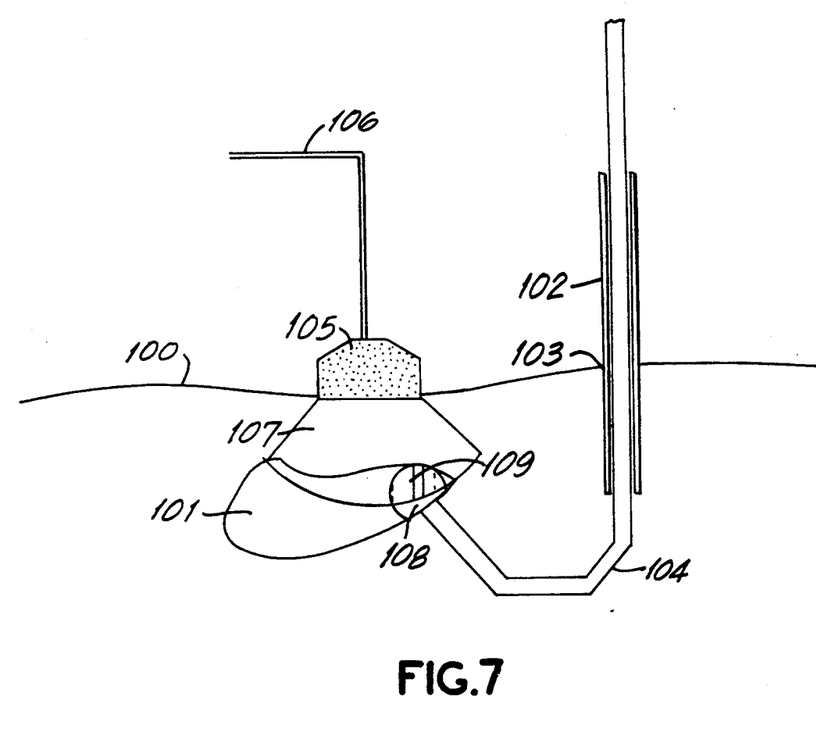
FIG. 7 is a side view of an embodiment using an exterior ultrasonic device.

The principles of the instant invention can also be applied in devices where the cooling probe and the ultrasonic source are not physically connected and integral. For instance, when a relatively large tissue cell mass needs to be freeze ablated, it may be difficult to use an ultrasonic transducer which is fitted on the head portion (tip) of a small probe used in catheters or laparoscopic procedures. In FIG. 7, within a biological structure having an external skin 100, part of an organ 101 needs to be freeze ablated. For instance, a large portion of a liver with cancer should be ablated. A laparoscopical procedure is chosen and a tubular penetrator 102 is inserted through a small skin incision 103. The dual lumen freezing catheter 101 is inserted through the tubular penetrator 102. A large area ultrasonic transducer (similar to that used for ultrasonic imaging except that the energy density of the beam can be an order of magnitude or more larger) is positioned above the pathological site on the outer skin. The operator must assure good acoustical conductivity between the transducer's head 105 and the target pathology. For instance, by assuring continuity of physiological structure in the beam's path. When the ultrasonic transducer 105 is actuated, it creates a fan-like field 107 within which the energy density is sufficient to cause nucleation is supercooled tissues. The dual lumen freezing catheter (without a transducer), when brought in contact with the cancer tissue cells, creates a spherical mass 108 which is supercooled sufficiently so that freezing can occur if embryonic nuclei can be formed. The hatched area 109 shows the space (volume) of congruence between the sufficiently supercooled mass 108 and the volume of sufficient ultrasonic energy density to cause nucleation.

A number of operational points should be taken into account. First, the ultrasonic transducer which is positioned extracorporeally can be moved to increase and optimize the space within which nucleation is feasible. In addition, a cone-shaped focused beam may be used instead of a fan-shaped beam. Second, the sizing, and the liquid flow rate through the dual lumen catheter should be adjusted upward to allow for the withdrawal of large amounts of heat released by the frozen tissues (heat of fusion). When used in this form, one may use an evaporative method of cooling using as the heat transfer liquid one of many available Freons and apply a partial vacuum on the outer lumen. When this approach is taken, there is introduced in the space between the outer lumen and the inner lumen a spiral wound spring (Micron Products, Fitchburg, Mass.) to prevent the collapse of the external lumen under vacuum. The spiral spring is made of a wire with a diameter of about 0.007" and a diameter of winding somewhat larger than the external lumen inner diameter. The spring is inserted under tension and when released it creates a force resisting the external pressure on the external lumen due to lumen evacuation. The heat of evaporation of most Freons is in the range of 50 calories/gr. and thus sufficiently high (at a flow rate of 100 ml/min.) to withdraw heat of fusion from a spherical mass about 2 cm in diameter. Lastly, some incomplete necrosis may occur in the space 108 not included in the space of ultrasonic effective influence 107, due to unavoidable intercellular freezing.

While we described specifically the use of a cardiac freeze ablation catheter and methods for ablating large masses when the ultrasonic source is extracorporeal in the foregoing detailed description, it should be understood that the principles and the operational modes described can be implemented in other catheters as well as in freeze ablation surgical probes and find uses in many additional procedures where a small area should be frozen and undergo necrosis. Such procedures are common in neurological, opthomological and a number of urological as well as gynecological practices.

The instant invention differs markedly from the cryogenic and ultrasonic ablation prior art. First, the prior art devices are not flexible freeze ablation catheters since it uses cryogenic temperatures and methods requiring stiff tubing. The classical definition of cryogenic temperatures are temperatures under −150° C. and that cryosurgery is usually defined as cooling tissues to temperatures below −60° C. (see, for instance, the 15th edition of the Encyclopedia Britannica Volume 3, pages 766–767), while in the instant invention tissues are cooled to a maximum of about −25° C. and the cooling medium lowest temperature is less than −50° C., which is far above the cryogenic range. The instant invention obtains well distributed nucleation of solid nuclei within the supercooled mass, and thus the ultrasonic frequencies utilized are much higher than in the prior art. In the present invention the wavelength of the ultrasonic beam is shorter than about 20 times the larger dimension of the cells in the target tissues (or in the range of 10 to 200 microns, corresponding to a frequency spectrum of 7.5

MHz to 150 MHz) and preferably 30–45 MHz. This assures that each cell has a sufficient pressure gradient to cause either cavitation nucleation by itself or nucleation due to the free energy differential induced by the ultrasonic wave pressure differential from site to site within a cell (microcavitation). The power density of the ultrasonic wave pressure at the target tissue cells is in the range of 1 to 500 milliwatts $cm^2$, preferably from about 10 to about 100 milliwatts $cm^2$.

I claim:

1. A catheter kit for the necrosis of tissue cells in a patient, comprising a catheter and ultrasonic cavitation means, said catheter comprising:
   (i) a first elongated tube adapted to flow tissue freezing fluid therein, said fluid being pumped from a source thereof external to said catheter, said first elongated tube having an imaginary axis and distal and proximal ends;
   (ii) a second elongated tube coaxial with the first elongated tube and spaced externally therefrom to form an annular space therebetween adapted to flow fluid therein, said second elongated tube having distal and proximal end;
   (iii) a head member connected to the distal ends of the first and second tubes and adapted to contact the tissue cells and apply freezing temperatures in the range of about $-10°$ C. to about $-50°$ C. to the contacted tissue cells to thereby freeze said tissue cells at the point of contact; the head member having fluid flow mens to receive the flow of freezing fluid and to be cooled therefrom;
   said ultrasonic cavitation means for generating an ultrasonic beam in the frequency range of from about 7.5 MHz to about 130 MHz to create a field coextensive with the tissue caused by the head portion to be at the freezing temperature, said ultrasonic beam having a power level of from about 1 milliwatt to about 300 milliwatts in the coextensive field; whereby the ultrasonic cavitation causes intracellular nucleation in the cells resulting in cell freezing and cell necrosis.

2. A catheter kit as in claim 1 wherein the first and second tubes are flexible and elastic.

3. A catheter kit as in claim 2 wherein the first and second tubes are round rings in cross-section, the second tube having an outer diameter and the outer diameter is less than 3 mm.

4. A catheter kit as in claim 1 wherein said ultrasonic cavitation means is a transducer which is part of the head member and the catheter including a source of electrical power and means for connecting the transducer to said power source.

5. A catheter kit as in claim 4 wherein the head member has a distal end tip portion and the transducer is part of the tip portion.

6. A catheter kit as in claim 1 wherein the first and second tubes are rigid and the catheter is a probe.

7. A catheter kit as in claim 1 wherein the ultrasonic cavitation means is connected to the head member and includes an ultrasonic transducer adapted to be applied to the skin of the patient.

8. A catheter kit as in claim 1 and further comprising:
   (i) a source of freezing fluid and pump means connected to the first and second tubes to cause the flow of the freezing fluid from said source through first and second tubes; and
   (ii) chiller means connected to the source to chill the freezing fluid to the range of from about $-10°$ C. to $-50°$ C.

9. A catheter kit as in claim 8 wherein the cavitation means includes:
   (i) a piezoelectric ultrasonic beam transducer connected as part of the head member;
   (ii) a pair of wire leads connected to the transducer and extending through at least a part of the length of the second tube; and
   (iii) an electronic oscillator means to produce ultrasonic waves, said oscillator means being connected to the wire leads.

10. A catheter kit as in claim 1 and including a thermoelectric cell means for cooling the fluid, said thermoelectric cell means being connected to said head member.

11. A catheter kit as in claim 10 wherein the thermoelectric cells means is positioned within the head member.

12. A catheter kit as in claim 1 wherein said second tube is round in cross-section and said head member is round in cross-section and has a larger outer diameter then the outer diameter of the second tube.

13. A catheter kit as in claim 1 wherein a freezing fluid is a liquid having a boiling point under $-10°$ C.

14. A catheter kit as in claim 1 wherein an elongated spiral spring is wound about the first tube and within the second tube.

15. A catheter kit as in claim 1 wherein the freezing fluid is a liquid having a boiling point under $-10°$ C. and further including vacuum means connected to the space between said first and second tubes to remove the heat of fusion by evaporating said liquid.

* * * * *